(12) United States Patent
Hosoi et al.

(10) Patent No.: US 6,547,563 B1
(45) Date of Patent: Apr. 15, 2003

(54) DENTAL TISSUE CONDITIONER AND KIT THEREFOR

(75) Inventors: Yasuhiro Hosoi, Tokuyama (JP); Osamu Iwamoto, Tokuyama (JP); Takaaki Imakura, Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 09/398,999

(22) Filed: Sep. 17, 1999

(30) Foreign Application Priority Data

Mar. 19, 1999 (JP) .............................. 11-076557

(51) Int. Cl.[7] .............................................. A61C 13/23
(52) U.S. Cl. ..................... 433/168.1; 523/120; 524/731
(58) Field of Search ....................... 433/168.1; 523/120, 523/731

(56) References Cited

U.S. PATENT DOCUMENTS

| | | | |
|---|---|---|---|
| 3,251,910 A | * | 5/1966 | Barnhart |
| 3,785,054 A | | 1/1974 | Van Handel |
| 4,661,065 A | * | 4/1987 | Gettleman ................ 433/168.1 |
| 4,788,240 A | | 11/1988 | Fujimoto |
| 4,970,245 A | * | 11/1990 | Futami et al. ............... 523/109 |
| 5,436,283 A | | 7/1995 | Okada et al. |
| 5,476,912 A | * | 12/1995 | Hosoi et al. .................. 526/279 |
| 5,513,987 A | * | 5/1996 | Hosoi et al. ............. 433/168.1 |
| 5,952,400 A | * | 9/1999 | Hosoi et al. ................. 523/120 |

FOREIGN PATENT DOCUMENTS

| | | |
|---|---|---|
| DE | 298 05 847 U | 5/1999 |
| EP | 0579132 A | 1/1994 |
| EP | 0614655 A | 9/1994 |
| GB | 1078207 | 8/1967 |

* cited by examiner

*Primary Examiner*—Ralph A. Lewis
(74) *Attorney, Agent, or Firm*—Birch, Stewart, Kolasch & Birch, LLP

(57) ABSTRACT

A method which comprises using silicone rubber as a material for dental tissue conditioner.

12 Claims, No Drawings

DENTAL TISSUE CONDITIONER AND KIT THEREFOR

DETAILED DESCRIPTION OF THE INVENTION

The present invention relates to a lining material for a denture base used in the dental treatment, particularly a dental tissue conditioner for a patient wearing a denture whose oral mucosa is deformed or inflamed, and to a kit therefor.

When a denture is used for a long time, it becomes gradually ill-fit with alveolar ridge because of, for example, the resorption of the alveolar ridge, whereby the denture becomes difficult to hold and loses stability. If the ill-fitting denture is continued to be used as it is, a non-uniform pressure is applied to the mucosa under the denture base, so that ulcer and/or inflammation may emerge on the mucosa or pain is caused by an occlusion pressure. Therefore, when the above ill-fitting occurs, it is necessary to prepare a new denture or to recover the fitness of the ill-fit denture for the mucosa by adjusting its base.

However, since the oral mucosa of the patient is unstable because of the ulcer and inflammation as described above, the preparation of a new denture or the adjustment of the denture base must not be done until the oral mucosa recovers to a normal condition, in order to secure the good fitness of the denture for the mucosa under the denture base.

The material used under such circumstances is a dental tissue conditioner. The dental tissue conditioner is continued to be used for lining the mucosa under the denture in use until the form and color of the mucosa recover to a normal condition.

Further, currently, the soft materials associated with the denture base are roughly classified by a denture adhesive, a dental tissue conditioner and a soft lining material. They are different from one another in the purpose, method and period of use, required properties and the like.

For example, the denture adhesive is used temporarily for such a short time as one day to a few days after applied by a patient himself. Therefore, the denture adhesive is required to show the adhesive strength to the extent of "sticking" rather than perfectly "bonding" to the denture base. On the other hand, the dental tissue conditioner and the soft lining material are the same in that they are applied by a dentist. However, they are quite different from each other in required physical properties because of the difference in the purposes of their use. Specifically, as described above, the dental tissue conditioner is used for treating the oral mucosa prior to the repair of the denture. Therefore, in view of the purpose, it must be flexible and plastically deformable, and the period of its use must be relatively short, for example, one week to a few weeks, until the oral mucosa recovers to a normal condition. On the contrary, since the soft lining material is used for repairing the denture, it must not be deformed for a long time after the repair of the denture.

Thus, all the above three types of materials are the same in that they are associated with the denture base, however, they are clearly divided into different groups as dental materials according to the purposes of their use and required properties.

Currently, as the dental tissue conditioner, there is widely used a mixed material that consists of a powder component comprising a polyethylmethacrylate or a copolymer thereof and a liquid component comprising a phthalate ester plasticizer containing about 4 to 20 wt % of ethanol. As for the tissue conditioner, a soft elastic product is obtained when the powder component and the liquid component are mixed together. Therefore, when the mucosa under the ill-fitting denture is lined with the material, it recovers the fitness of the denture and relieves the pain caused by the occlusion pressure. Further, when the pain is relieved, the ulcer or inflammation of the oral mucosa gradually disappears and, at the same time, the form of the oral mucosa recovers to its normal condition with time. At this point, the tissue conditioner shows an excellent characteristic that it deforms along with the change in the deformation of the oral mucosa.

However, the conventional dental tissue conditioner as described above has the following problems (1) to (3).

(1) The elution of the plasticizer and ethanol during the use of the conditioner deteriorates the conditioner with time, raises a concern for a possible influence upon a living body and causes an unpleasant taste and irritation. (2) The conditioner becomes dirty or gives off an odor by absorbing oils contained in foods, saliva and the like, during its use. (3) It is necessary to remove a spent dental tissue conditioner from the denture base for the application of the lining material after the treatment of the ailments; at this point, however, it is extremely difficult to remove (specifically, by grinding) the dental tissue conditioner which is firmly stuck on the denture base because the conditioner is made of basically the same material as that of the denture base.

It is an object of the present invention to provide a dental tissue conditioner which has overcome the above problems (1) to (3).

Other objects and advantages of the present invention will be apparent from the following description.

That is, the present inventors have made intensive studies to overcome the above problems and succeeded in obtaining a dental tissue conditioner which has no such problems as the above (1) to (3) by using a silicone rubber which has not been used heretofore for a dental tissue conditioner, particularly a room-temperature addition-polymerization-type silicone rubber, as a material. Thus, the present invention has been completed.

According to the present invention, the above objects and advantages of the present invention are achieved by a method which comprises using a silicone rubber as a material for a dental tissue conditioner.

The "silicone rubber" as used herein means a crosslinked organopolysiloxane. Further, a visco-elastic body obtained by uniformly dispersing fillers and various additives in the silicone rubber is called a "silicone rubber composition".

A silicone rubber is a material having excellent characteristics as a dental material, such as repellency, non-cohesiveness and non-toxicity to a living body. A dental tissue conditioner which is substantially formed of a silicone rubber has not been known heretofore.

The dental tissue conditioner according to the present invention substantially comprises a silicone rubber whose main components are colorless, tasteless, odorless, non-volatile and non-toxic. Therefore, basically, it does not have the above problems (1) and (2). Further, since the silicone rubber is different from the resin used in the denture base, it is possible to design an adhesive which has a controlled adhesive force to the resin. Thus, the above problem (3) can also be solved.

The dental tissue conditioner of the present invention has an advantage that it can be directly formed in a mouth if the silicone rubber is a room-temperature addition-polymerization-type silicone rubber.

Further, the dental tissue conditioner of the present invention shows an excellent performance as a dental tissue conditioner that it can be moderately plastically deformed with moderate elasticity retained as the damaged mucosa under the denture base heals, when a silicone rubber composition to be used has (i) an elastic strain of preferably 15% or more, more preferably 20% or more, and a permanent strain of preferably 0.5% or more, (ii) a loss tangent of preferably 0.5 or more, or (iii) a Shore A hardness of preferably 15 or less.

Such physical properties can be attained by controlling the crosslinking density of a silicone rubber, the amount of a silicone resin filler, a silica filler or other filler as a reinforcing material, and the like.

Any filler which is generally added to a silicone rubber can be used as the above filler without any restriction. Illustrative examples of the fillers include a silica filler such as pulverized quartz, fused silica powder, colloidal silica powder and fumed silica powder; a silicone resin filler such as polymethylsilsesquioxane powder, polyphenylsilsesquioxane powder and poly(3,3,3-trifluoropropyl) silsesquioxane powder; a fluorocarbon resin filler such as polytetrafluoroethylene powder and polyvinylidenefluoride powder; other polymer powder; carbon black; glass fiber; a composite filler (a ground composite of inorganic oxides and polymers); and the like.

Illustrative examples of the above various additives include a hydrogen gas absorbent such as platinum black or particulate palladium; a reaction controller such as 1,3-divinyltetramethyldisiloxane; an ultraviolet absorber such as 2,4-dihydroxybenzophenone; a pigment such as titanium dioxide; an antioxidant such as BHT; an antibacterial agent such as chitosan; a plasticizer such as silicone oil; and the like.

The various fillers and additives other than the above silicone resin filler and the above silica filler are added as required according to purposes.

The dental tissue conditioner of the present invention substantially comprises a silicone rubber. Therefore, its properties are substantially determined by the physical properties of a silicone rubber to be used.

The silicone rubber used in the present invention is not particularly limited as long as it satisfies the flexibility and deformability required for a dental tissue conditioner. The silicone rubber of high-temperature vulcanizing type, condensation type or addition-polymerization type can be used. However, the condensation-type or addition-polymerization-type silicone rubber which can be polymerized at room temperature is preferable because it can be polymerized and cured in a desired form in a mouth and directly used as a dental tissue conditioner.

Above all, a room-temperature addition-polymerization-type silicone rubber is particularly preferable because it does not produce a by-product during a curing reaction and shows excellent durability when used in a mouth.

When the silicone rubber composition used in the present invention has an elastic strain of preferably 15% or more, more preferably 20% or more, a permanent strain of preferably 0.5% or more, a loss tangent of preferably 0.5 or more and a Shore A hardness of preferably 15 or less, it shows an excellent property that it gives almost no pain to a patient and deforms in correspondence with the form of the mucosa under the denture base without hindering the recovery of the form of the mucosa, when used as the material for the tissue conditioner.

The "elastic strain" and the "permanent strain" as used herein are values measured in accordance with JIS T6513-1991 using a sample prepared in accordance with the sample preparing condition of ISO 10139-1 (Dentistry-Resilient lining materials for removable dentures—Part 1:Short-term materials).

The "loss tangent" (tan δ) is a value measured by a dynamic visco-elastic measuring device at 37° C. and 1 Hz and under a tensile load using a sample prepared in the same manner as the above sample.

The "Shore A hardness" is a value measured in accordance with JIS K6301-1975 using a sample prepared in the same manner as the above sample.

The silicone rubber composition used in the present invention more preferably has an elastic strain of 25% to 40%, a permanent strain of 0.7% to 5%, and a Shore A hardness of 3 to 12. The silicone rubber composition used in the present invention more preferably has a loss tangent of 0.7 to 1.2.

The silicone rubber used in the present invention is preferably a cured product of the following uncured composition, from the viewpoints that it can be polymerized and cured in a desired form in the mouth of a patient, that the obtained silicone rubber can be directly used as the dental tissue conditioner of the present invention and that it does not produce a harmful by-product.

A cured product of an uncured composition, which comprises:
  (A) an organopolysiloxane having at least two organic groups having a terminal carbon-carbon unsaturated bond in the molecule,
  (B) an organohydrogenpolysiloxane having at least three hydrogen atoms, which are directly bonded to silicone atoms, in the molecule, and
  (D) a hydrosilylation catalyst;
the ratio of the total number of the hydrogen atoms, which are directly bonded to silicone atoms, of the component (B) to the total number of the terminal carbon-carbon unsaturated bonds of the component (A) being 0.2 to 1.5.

When the reaction of the uncured composition into the cured product is carried out in the mouth of a patient, the cured product is directly used as the dental tissue conditioner of the present invention.

In the above uncured composition, the crosslinking density of the cure product is adjusted by controlling the ratio of the amount of the component (A) to the amount of the component (B), whereby the flexibility and plastic deformability (physical properties such as elastic strain, permanent strain, loss tangent and Shore A hardness) of the silicone rubber as the obtained cured product can be adjusted. The above component (B) functions as a crosslinking agent which crosslinks the component (A), and the component (D) functions as a catalyst for a hydrosilylation reaction which is a crosslinking reaction. Although the above adjustment is still possible only by controlling the ratio of the amount of the component (A) to the amount of the component (B), the reaction may be carried out in the co-presence of an organohydrogenpolysiloxane (component (E)) having one or two hydrogen atoms, which are bonded to silicone atoms, in the molecule. The above adjustment is further facilitated when the reaction is carried out in the co-presence of the component (E).

In this case. the silicone rubber is preferably a cured product of an uncured composition which comprises:
  (A) an organopolysiloxane having at least two organic groups having a terminal carbon-carbon unsaturated bond in the molecule,
  (B) an organohydrogenpolysiloxane having at least three hydrogen atoms, which are directly bonded to silicone atoms, in the molecule, (D) a hydrosilylation catalyst, and
(E) an organohydrogenpolysiloxane having one or two hydrogen atoms, which are directly bonded to silicone atoms, in the molecule;

the ratio of the total number of the hydrogen atoms, which are directly bonded to silicone atoms, of the component (B) and the hydrogen atoms, which are directly bonded to silicone atoms, of the component (E) to the total number of the terminal carbon-carbon unsaturated bonds of the component (A) being 0.5 to 5; and the ratio of the total number of the hydrogen atoms, which are directly bonded to silicone atoms, of the component (E) to the total number of the hydrogen atoms, which are directly bonded to silicone atoms, of the component (B) being 0.5 to 10.

As described above, the substantial physical properties of the dental tissue conditioner of the present invention are determined by a silicone rubber used. Therefore, by controlling the ratio of the amount of the component (A) to the amount of the component (B), and as required, to the amount of the component (E) in the above uncured composition, a suitable viscoelasticity can be attained as the dental tissue conditioner. The "suitable viscoelasticity as the dental tissue conditioner" referred to herein means having both an adequate elasticity for relieving the pain and an adequate viscosity (flowability) which follows the deformation of the mucosa at the same time and in well balance. The above elastic strain, permanent strain, loss tangent, Shore A hardness and preferable ranges thereof are ones proposed by the present inventors for the first time as the indice for indicating a preferable viscoelasticity as the dental tissue conditioner.

The above uncured composition will be described in detail hereinafter. For the sake of convenience In description, "organopolysiloxane having at least two organic groups having a terminal carbon-carbon unsaturated bond in the molecule" and "organohydrogenpolysiloxane having hydrogen atoms, which are directly bonded to silicone atoms (and which correspond to SiH groups), in the molecule" may also be referred to simply as "unsaturated bond-containing siloxane" and "SiH siloxane", respectively.

The component (A) used in the above uncured composition is an organopolysiloxane having at least two organic groups having a terminal carbon-carbon unsaturated bond in the molecule. The structure of the organopolysiloxane is not limited and may be a straight chain, a branched chain or a mixture thereof.

The viscosity thereof is not particularly limited but is preferably 10 to 10,000 poise from the viewpoints of the properties of the uncured paste, the properties of the cured product, and the like. The viscosity is more preferably 10 to 3,000 poise. However, when several types of unsaturated bond-containing siloxanes are mixed together to be used as the component (A), the above viscosity indicates the viscosity of the resulting mixture.

Preferable examples of the organic groups having a carbon-carbon unsaturated bond at the terminal which exist in the molecules of the unsaturated bond-containing siloxane as the component (A) include a vinyl group, allyl group, 1-butenyl group, ethynyl group and the like. Of these, the vinyl group is the most preferable in view of synthesis and availability. These organic groups having a carbon-carbon unsaturated bond at the terminal may exist either at the terminal or the middle of the chain of the organosiloxane or at both. It is preferable for the sake of having the reactivity at the time of curing and the excellent physical properties of the cured product that at lease one of the organic groups exist at the terminal.

Illustrative examples of organic groups other than the above "organic groups having an unsaturated bond at the terminal", which exist in the molecules of the unsaturated bond-containing siloxane as the component (A), include an alkyl group such as methyl group, ethyl group, propyl group, butyl group and octyl group; an aryl group such as a phenyl group; a substituted alkyl group such as a chloromethyl group and 3,3,3-trifluoropropyl group; and the like. Of these, the methyl group is the most preferable because it is easy to synthesize and obtain and provides the cured product with excellent physical properties.

Specific and typical examples of the component (A) that can be used in the present invention include organopolysiloxanes represented by the following formulae:

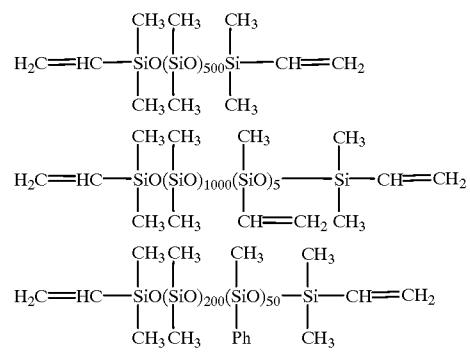

(wherein Ph is a phenyl group, which is also applicable in the following description). The order of bonding of the recurring units of the above compounds and the compounds used in the following Examples and Comparative Examples is utterly arbitrary, and the number of the recurring units shown in the structural formula is merely the total amount of each structural unit.

The component (B) used in the present invention is an organohydrogenpolysiloxane having at least three hydrogen atoms, which are directly bonded to silicone atoms, in the molecule, and it functions to crosslink the unsaturated bond-containing siloxane as the above component (A) to give a rubber elastic body.

In order to form a crosslinked structure by the reaction with the unsaturated bond-containing siloxane, the organohydrogenpolysiloxane must have at least three hydrogen atoms directly bonded to silicone atoms (that is, SiH groups) in the molecule. If the number of the SiH groups existent in the molecule is less than 3, the crosslinked structure cannot be formed, with the result that the rubber elastic body cannot be obtained.

The organic groups existent in the molecules of the SiH siloxane of the component (B) are not particularly limited and are exemplified by the same organic groups as the organic groups other than the "organic groups having a terminal carbon-carbon unsaturated bond" which exist in the molecules of the unsaturated bond-containing siloxane as the above component (A). The methyl group is the most preferable because it is easy to synthesize and obtain and provides the cured product with excellent physical properties. The SiH siloxane may be a straight chain, a branched chain, a ring or a mixture thereof.

Specific examples of the component (B) that can be used in the present invention include the organohydrogenpolysiloxanes represented by the following formulae:

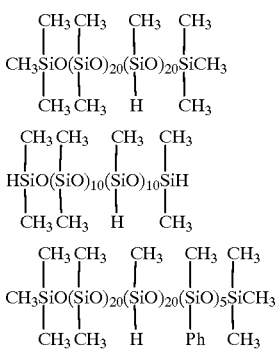

As is the case of the unsaturated bond-containing siloxane as the component (A), the order of bonding of the recurring units in the molecule of the above compound and the SiH siloxane of the component (B) used in the following Examples and Comparative Examples is utterly arbitrary, and the number of the recurring units shown in the structural formula is merely the total amount of each structural unit.

The component (E) which may be reacted in the co-presence of the component (A) and the component (B) in the above uncured composition is an organohydrogenpolysiloxane having only one or two hydrogen atoms directly bonded to silicone atoms in the molecule. When the component (E) is mixed, the elasticity tends to be low, thereby facilitating the adjustment of the viscoelasticity of the cured product.

Specific examples of the component (E) that can be used in the present invention include the organohydrogenpolysiloxanes represented by the following formulae:

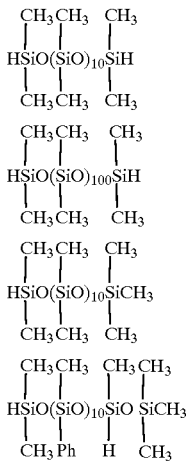

As is the case of the unsaturated bond-containing siloxane as the component (A), the order of bonding of the recurring units in the molecule of the above compounds and the SiH siloxane of the component (E) used in the following Examples and Comparative Examples is utterly arbitrary, and the number of the recurring units shown in the structural formula is merely the total amount of each structural unit.

When the component (E) is not used in the above uncured composition, a cured product having a preferable viscoelasticity as the above dental tissue conditioner can be obtained, when the amount ratio of the total number of the hydrogen atoms, which are directly bonded to silicone atoms, of the component (B) to the total number of the terminal carbon-carbon unsaturated bonds of the component (A) is 0.2 to 1.5, particularly preferably when the amount ratio is 0.3 to 1.2.

As for the composition containing the component (E), the ratio of the total number of the hydrogen atoms, which are directly bonded to silicone atoms, of the component (B) and the hydrogen atoms, which are directly bonded to silicone atoms, of the component (E) to the total number of the terminal carbon-carbon unsaturated bonds of the component (A) is 0.5 to 5, preferably 0.7 to 2, and the ratio of the total number of the hydrogen atoms, which are directly bonded to silicone atoms, of the component (E) to the total number of the hydrogen atoms, which are directly bonded to silicone atoms, of the component (B) is 0.5 to 10, preferably 2 to 10.

The hydrosilylation catalyst as the component (D) used in the present invention functions as a catalyst that causes a reaction (specifically, a hydrosilylation reaction) among the component (A), the component (B), and the component (E) which is added as required, to form a matrix formed of the crosslinked organosiloxane. Any catalyst that is generally used as a hydrosilylation catalyst can be used as the component (D) without restriction as long as it has such a catalytic function.

Illustrative examples of the catalyst that is preferably used as the component (D) include a platinum catalyst such as chloroplatinic acid, alcohol-modified product thereof and a vinylsiloxane complex of platinum, or a rhodium catalyst similar to these platinum catalysts. Of these, the platinum catalyst is preferable in view of availability and the like. To enhance the storage stability, it is preferable to use the vinylsiloxane complex of platinum which has a low chlorine content.

The mixing amount of the component (D) is not particularly limited as long as it can fully promote the hydrosilylation reaction. Generally speaking, the reaction rate of the hydrosilylation reaction increases to some extent as the mixing amount of the component (D) increases. However, the use of the component (D) in an excessive amount does not produce an effect that matches the excess thereof and causes an economical disadvantage and, what is worse, it makes it difficult to control the crosslinking reaction and causes problems such as coloration. Therefore, the mixing amount of the component (D) should be properly determined according to a system in the above respects. By the way, when the component (D) is a platinum catalyst, the preferable mixing amount of the component (D), as platinum, for example, is 0.1 to 1,000 ppm based on the total amount of the component (A) and the component (B) (and the component (E) when it is used).

The above uncured composition of the present invention further contains at least one filler (C) selected from the group consisting of silicone resin particles and silica particles. The component (C) functions as a reinforcement to provide the silicone rubber with mechanical strength.

In this case, the silicone rubber composition is preferably a cured product of an uncured composition which comprises:
(A) an organopolysiloxane having at least two organic groups having a terminal carbon-carbon unsaturated bond in the molecule,
(B) an organohydrogenpolysiloxane having at least three hydrogen atoms, which are directly bonded to silicone atoms, in the molecule,
(C) at least one filler selected from the group consisting of silicone resin particles and silica particles, and
(D) a hydrosilylation catalyst;
the ratio of the total number of the hydrogen atoms, which are directly bonded to silicon atoms, of the component (B) to the total number of the terminal carbon-carbon unsaturated bonds of the component (A) being 0.2 to 1.5; the component (C) being contained in an amount of 1 to 300 parts by weight per 100 parts by weight of the component (A); and the component (D) being contained in a catalytic amount, or, a cured product of an uncured composition which comprises:

(A) an organopolysiloxane having at least two organic groups having a terminal carbon-carbon unsaturated bond in the molecule, (B) an organohydrogenpolysiloxane having at least three hydrogen atoms, which are directly bonded to silicone atoms, in the molecule, (C) at least one filler selected from the group consisting of silicone resin particles and silica particles, (D) a hydrosilylation catalyst, and (E) an organohydrogenpolysiloxane having one or two hydrogen atoms, which are directly bonded to silicone atoms, in the molecule;

the ratio of the total number of the hydrogen atoms, which are directly bonded to silicone atoms, of the component (B) and the hydrogen atoms, which are directly bonded to silicone atoms, of the component (E) to the total number of the terminal carbon-carbon unsaturated bonds of the component (A) being 0.5 to 5; the ratio of the total number of the hydrogen atoms, which are directly bonded to silicone atoms, of the component (E) to the total number of the hydrogen atoms, which are directly bonded to silicone atoms, of the component (B) being 0.5 to 10; the component (C) being contained in an amount of 1 to 300 parts by weight per 100 parts by weight of the component (A); and the component (D) being contained in a catalytic amount.

The component (C) used in the above uncured composition functions as a reinforcement for the silicone rubber, which is a cured product obtained from the unsaturated bond-containing siloxane, the SiH siloxane and the hydrosilylation reaction catalyst material.

As the component (C), a silicone resin filler such as polymethylsilsesquioxane powder, polyphenylsilsesquioxane powder and poly(3,3,3-trifluoropropyl)silsesquioxane powder and a silica filler such as pulverized quartz, fused silica powder, colloidal silica powder and fumed silica powder can be used without restriction.

Of the fillers enumerated as the component (C) of the present invention, the silicone resin filler has high conformity with silicone as a matrix because it has Si—O bonds and Si—CH$_3$ bonds, and it also shows a reinforcing effect to the silicone rubber, whereby the cured product can have some mechanical strength. Further, by selecting the silicone resin filler having an appropriate particle diameter, it becomes possible to fill the filler at a high filling ratio and, in addition, it can provide the cured product with machinability because it can provide the cured product with sufficient rigidity.

Further, of the fillers enumerated as the component (C) of the present invention, the silica filler provides a reinforcing effect when contained in the uncured composition. It is assumed that this is because hydrogen bonds are produced near the surface of the silica filler when the silica filler is mixed with the silicone rubber matrix having a small intermolecular force and it gives a partially crystallized structure.

The mixing amount of the component (C) is not particularly limited as long as it enables the component (C) to fully function as a reinforcing filler. The mixing amount is 1 to 300 parts by weight, preferably 5 to 100 parts by weight, based on 100 parts by weight of the component (A) in view of the reinforcing effect and the operability of the uncured paste.

The above additives are mixed together before the curing (crosslinking) reaction is carried out.

The above uncured composition is generally produced by preparing a kit in which the component (B) and the component (E) are preserved separately from the component (D) (which implies that a hydrosilylation reaction does not take place during preservation), for example, a two-paste-type kit which comprises a composition containing the component (A), the component (B), the component (C), the component (E) as required, and various additives and another composition containing the component (A), the component (C), the component (D) and various additives, or a paste-and-liquid-type kit, and the like; and mixing the two compositions to cause a crosslinking reaction right before the use of the uncured composition.

The above kit is provided to the operator in preparing the dental tissue conditioner of the present invention. Therefore, in some cases, the kit itself or the two compositions constituting the kit (or a composition obtained by mixing the two compositions) is referred to as the dental tissue conditioner. In the present specification, the kit is called "a dental tissue conditioner kit" or "an uncured composition for a dental tissue conditioner kit" and the cured product obtained after the reaction is called "a dental tissue conditioner".

The dental tissue conditioner kit that can be preferably used in the above preparation may be the following kit (I) or (II).

(I) A dental tissue conditioner kit comprising a combination of a first uncured composition component (COMP-1) and a second uncured composition component (COMP-2) which satisfy the following conditions (1), (2) and (3):

(1) The COMP-1 and the COMP-2 contain at least one component selected from the component (A), the component (B), the component (C), and the component (D).

(2) The combination of the COMP-1 and the COMP-2 contains all the above components (A) to (D).

(3) The component (B) and the component (D) coexist neither in the COMP-1 nor in the COMP-2.

(II) A dental tissue conditioner kit comprising a combination of a first uncured composition component (COMP-3) and a second uncured composition component (COMP-4) which satisfy the following conditions (1), (2) and (3):

(1) The COMP-3 and the COMP-4 contain at least one component selected from the component (A), the component (B), the component (E), the component (C) and the component (D).

(2) The combination of the COMP-3 and the COMP-4 contains all the above components (A) to (D) and the above component (E).

(3) The component (D) coexists with the component (B) and the component (E) neither in the COMP-3 nor in the COMP-4.

In the above dental tissue conditioner kits, fillers and additives other than the silicone resin particle filler and/or the silica particle filler may be suitably added to the first uncured composition component and the second uncured composition component that constitute the kits, as long as the kits satisfy the conditions (1) to (3).

The preferable dental tissue conditioner kit of the present invention has a first uncured composition component comprising:

(A) an organopolysiloxane having at least two organic groups having a terminal carbon-carbon unsaturated bond in the molecule, (B) an organohydrogenpolysiloxane having at least three hydrogen atoms, which are directly bonded to silicone atoms, in the molecule, and optionally, (E) an organohydrogenpolysiloxane having one or two hydrogen atoms, which are directly bonded to silicone atoms, in the molecule, and a second uncured composition component comprising:

(A) an organopolysiloxane having at least two organic groups having a terminal carbon-carbon unsaturated bond in the molecule, and (D) a hydrosilylation catalyst filled in separate containers; and at least one of the first uncured composition component and the second uncured composition component contains:

(C) at least one filler selected from the group consisting of silicone resin particles and silica particles. In this case, both the first uncured composition component and the second uncured composition component are more preferably a paste.

The method of preparing the uncured composition components that constitute the dental tissue conditioner kit is not particularly limited. They can be prepared by selecting necessary components from the component (A), the component (B), the component (C), the component (D), the component (E), fillers and additives, measuring the required amounts thereof, and kneading them using a general mixer such as kneader or planetary or a general agitator until the mixture is uniform to obtain the components in the form of a paste or liquid.

The dental tissue conditioner of the present invention is prepared by measuring the predetermined amounts of the above two uncured composition components right before its use, mixing the components, applying the resulting mixture to the denture base to which an adhesive has already been applied, holding the denture in the mouth of a patient until the mixture is fully cured, taking the denture out of the mouth after the mixture is cured and removing extra portions.

As the above adhesive, the silicone-modified acrylic copolymer adhesive disclosed in JP-A 7-70246 or JP-A 7-76611 is preferably used.

Examples will be given below to further illustrate the present invention. The present invention shall not be limited thereto, however.

The organopolysiloxanes used in the following Examples are shown in Table 1.

TABLE 1 organopolysiloxanes $$R-\underset{\underset{CH_3}{|}}{\overset{\overset{CH_3}{|}}{Si}}O(\underset{\underset{CH_3}{|}}{\overset{\overset{CH_3}{|}}{Si}}O)_x(\underset{\underset{H}{|}}{\overset{\overset{CH_3}{|}}{Si}}O)_y\underset{\underset{CH_3}{|}}{\overset{\overset{CH_3}{|}}{Si}}-R$$

| component | compound No. | R | x | y | viscosity (poise) |
|---|---|---|---|---|---|
| A | a1 | —CH=CH$_2$ | 700 | 0 | 100 |
|   | a2 | —CH=CH$_2$ | 1000 | 0 | 1000 |
|   | a3 | —CH=CH$_2$ | 1400 | 0 | 1700 |
| B | b1 | —CH$_3$ | 20 | 20 | 0.3 |
|   | b2 | —CH$_3$ | 40 | 10 | 0.4 |
| E | e1 | —H | 10 | 0 | 0.04 |
|   | e2 | —H | 30 | 0 | 0.05 |

The fillers used in the following Examples are shown in Table 2.

TABLE 2 fillers

| component | compound No. | material | particle diameter ($\mu$m) |
|---|---|---|---|
| C | c1 | polymethylsilsesquioxane | 2 |
|   | c2 | polyphenylsilsesquioxane | 5 |
|   | c3 | surface-treated fumed silica | 8 |
|   | c4 | fused silica | 10 |

In the following Examples and Comparative Examples, the dental tissue conditioner was evaluated in the following methods. The same sample was measured for three times and the average value of the measurements was taken.

(1) loss tangent (tan δ): A strip-shaped cured product was prepared, kept in water of 37° C. for two hours and then measured for a loss tangent at 37° C. and 1 Hz and under a tensile load using a dynamic visco-elastic measuring device. The "loss tangent" means the ratio of the storage elastic modulus to the loss elastic modulus of the cured product. The larger the loss tangent, the more viscoelastic the cured product. The tissue conditioner that can be preferably used has a loss tangent of 0.5 or more.

(2) elastic strain: A cured product having a diameter of 13 mm and a height of 20 mm was prepared, kept in water of 37° C. for two hours, left to stand in the room of 23° C. for five minutes and then measured for an elastic strain in accordance with the following method.

Firstly, the height (A) of the cured product after a load of 10 kPa was applied thereon for 30 seconds was measured. Then, after 30 seconds, an additional load was applied thereon over 10 seconds in such an amount that the total load was to be 100 kPa, and after 30 seconds from the end of the application of the load, the height (B) of the cured product was measured. The elastic strain was calculated from the following expression with these measurements.

$$\text{elastic strain }(\%)=\{(A-B)/20\}\times 100$$

The tissue conditioner that can be preferably used has an elastic strain of 15% or more. Since an elastic strain of 40% or higher cannot be measured by this method, values equal to or higher than 40% are all expressed as 40%.

(3) permanent strain: A cured product having a diameter of 13 mm and a height of 20 mm was prepared, kept in water of 37° C. for two hours, left to stand in the room of 23° C. for five minutes and then measured for a permanent strain in accordance with the following method.

Firstly, the height (C) of the cured product after a load of 4 kPa was applied thereon for 25 seconds was measured. Then, after a distortion of 12% (2.4 mm) was given thereto over 5 seconds, the cured product was held for 30 seconds. After it was left to stand without loads for 30 seconds, a load of 4 kPa was applied thereon again, and the height (D) thereof after 30 seconds was measured. The permanent strain was calculated from the following expression with these measurements.

$$\text{permanent strain }(\%)=\{(C-D)/20\}\times 100$$

The tissue conditioner that can be preferably used has a permanent strain of 0.5% or more.

(4) Shore A hardness: A cured product having a diameter of 9 mm and a height of 12 mm was prepared and kept in water of 37° C. for two hours. Then, after the cured product was left to stand in the room of 23° C. for five minutes, a load of 9.8 N was applied thereon using a spring-type hardness tester (type A). The value after 30 seconds from the application of the load was taken as the Shore A hardness of the cured product. The tissue conditioner that can be preferably used has a Shore A hardness of 15 or less.

(5) degree of coloration: A cured product having a size of 10 mm×10 mm×2 mm was prepared, kept in water of 37° C. for two hours, and then measured for L*, a* and b* before coloration using a color-difference meter. Thereafter, the test piece was immersed in a 5 wt % coffee aqueous solution and kept therein at 40° C. for 24 hours under agitation. After that, the test piece was washed with water, dried, and measured for the L*, a* and b* using the color-difference meter again. The degree of coloration (ΔE*) was calculated from the following expression with the differences ΔL*, Δa* and Δb*.

degree of coloration $(\Delta E^*) = \{(\Delta L^*)^2 + (\Delta a^*)^2 + (\Delta b^*)^2\}^{1/2}$ (6) stabilities of physical properties with time: The elastic strain, permanent strain and Shore A hardness of a sample, which had been kept in water of 37° C. for seven days, were measured in accordance with the above methods (2), (3) and (4).

(7) evaluation of degree of ease of removal from denture base: An adhesive was applied on a resin plate, which had been prepared in the same manner as the denture base, and the dental tissue conditioner was applied on the adhesive-coated surface and cured. The plate was kept in water of 37° C. for one week, and the dental tissue conditioner was then removed from the plate with a knife, a dental rotary grinder and the like. The degree of ease of the removal was evaluated in three levels, which are "A: easily removable only with a knife", "B: a grinder required for removal of some portions" and "C: removable only with a grinder". In the evaluation, "A" meant "excellent" while "C" meant "poor". A 0.5 wt % methylene chloride solution of a copolymer having the average composition represented by the following formula was used as the adhesive for the dental tissue conditioner of the present invention, while no adhesive was used for the acrylic tissue conditioner.

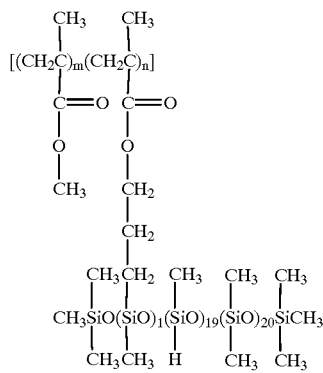

wherein m is 1,000 and n is 10.

(8) test of machinability: A cured product having a diameter of 9 mm and a length of 12 mm was prepared and kept in water of 37° C. for 24 hours. Then, the cured product was measured for machinability using a dental microengine, a carbide bar and a silicone point. The evaluation was made in accordance with the following criterion consisting of the levels A to C.

A: Surface portion as well as edge portion was abraded.

B: Only edge portion was abraded.

C: Not abraded.

EXAMPLE 1

Each of the compounds a1, a3 and c1 shown in Tables 1 and 2 and titanium dioxide were charged into a planetary in amounts of 50 parts by weight and 1 part by weight, respectively, and a vinylsiloxane complex of platinum was also charged into the planetary in such an amount that platinum was to be 100 ppm based on the total amount of the compounds a1 and a3. The resulting mixture was mixed until it became uniform and named as a "paste (I)".

The compounds a1, a3, b2 and c1 shown in Tables 1 and 2 were charged into a planetary in amounts of 50 parts by weight, 50 parts by weight, 2.5 parts by weight and 50 part by weight, respectively. The resulting mixture was mixed until it became uniform and named as a "paste (II)".

The paste (I) and the paste (II) were mixed in a mixing ratio of 1:1. The resulting mixture was evaluated in accordance with the above evaluation method. The result is shown in Table 3.

EXAMPLES 2 to 10

The materials of each composition shown in Tables 3 and 4 were mixed in a planetary in the same manner as in Example 1 to prepare pastes. The platinum catalyst used was the same as one used in Example 1.

A test was made on each of the pastes in accordance with the above evaluation method. The results are shown in Tables 3 and 4.

TABLE 3

|  | Example 1 | Example 2 | Example 3 | Example 4 | Example 5 |
|---|---|---|---|---|---|
| (I) component (A) | a1 50 a3 50 | a2 100 | a1 25 a3 75 | a1 50 a3 50 | a1 25 a3 75 |
| component (C) | c1 50 | c1 30 | c2 30 | c1 50 | c2 30 |
| component (D) (ppm) | 100 | 100 | 50 | 100 | 50 |
| other component | TiO2 pigment 1 |  |  | TiO2 pigment 1 |  |
| (II) component (A) | a1 50 a3 50 | a2 100 | a1 50 a3 50 | a1 50 a3 50 | a1 50 a3 50 |
| component (B) (H/V ratio) | b2 2.5 (1.0) | b2 2.0 (0.8) | b1 0.4 (0.3) | b2 3 (1.2) | b1 2.5 (0.3) |
| component (E) (H/V ratio) | 0 (0.0) | 0 (0.0) | e1 1.8 (0.7) | 0 (0.0) | e1 2.3 (0.9) |
| total H/V ratio | (1.0) | (0.8) | (1.0) | (1.2) | (1.2) |
| component (C) | c1 50 | c1 30 | c2 30 | c1 50 | c2 30 |
| other copponent |  |  |  |  |  |
| mixing ratio ((I)/(II)) | 1:1 | 1:1 | 1:1 | 1:1 | 1:1 |
| tan δ | 0.7 | 1.0 | 0.8 | 0.6 | 0.8 |
| elastic   initial value | 35 | >40 | 30 | 27 | 26 |
| strain (%)   value after 7 days | 34 | >40 | 28 | 26 | 24 |
| permanent   initial value | 2.7 | 4.8 | 2.1 | 1.6 | 1.7 |
| strain (%)   value after 7 days | 2.5 | 4.5 | 1.9 | 1.5 | 1.5 |
| Shore A   initial value | 9.1 | 5.7 | 7.7 | 11.6 | 9.4 |
| hardness   value after 7 days | 9.1 | 5.8 | 7.8 | 11.7 | 9.4 |
| degeee of coloration (ΔE*) | 7.9 | 8.9 | 8.4 | 9.0 | 8.6 |
| removability | A | A | A | A | A |
| machinability | A | A | A | A | A |

TABLE 4

|  | Example 6 | Example 7 | Example 8 | Example 9 | Example 10 |
|---|---|---|---|---|---|
| (I) component (A) | a1 50 a3 50 | a2 100 | a1 50 a3 50 | a2 100 | a1 25 a3 75 |
| component (C) | c1 50 c3 10 | c1 30 c4 10 | c3 15 | c1 30 | c1 20 c3 10 |
| component (D) (ppm) | 100 | 100 | 100 | 100 | 50 |
| other component | TiO2 pigment 1 |  | TiO2 pigmerit 1 |  |  |
| (II) component (A) | a1 50 a3 50 | a2 100 | a1 50 a3 50 | a2 100 | a1 50 a3 50 |
| component (B) (H/V ratio) | b2 2.5 (1.0) | b2 2.0 (0.8) | b2 2.3 (0.7) | b2 2.0 (0.5) | b1 0.8 (0.6) |
| component (E) (H/V ratio) | 0 (0.0) | 0 (0.0) | 0 (0.0) | e1 2.6 (1.0) | e2 0.9 (0.7) |
| total H/V ratio | (1.0) | (0.8) | (0.7) | (1.5) | (1.3) |
| component (C) | c1 50 c3 10 | c1 30 c4 10 | c3 15 | c1 30 | c1 20 c3 10 |
| other component |  |  |  |  |  |
| mixing ratio ((I)/(II)) | 1:1 | 1:1 | 1:1 | 1:1 | 1:1 |
| tan δ | 0.7 | 1.0 | 0.7 | 0.8 | 0.8 |
| elastic   initial value | 33 | 38 | >40 | 34 | 23 |
| strain (%)   value after 7 days | 32 | 36 | >40 | 33 | 21 |
| permanent   initial value | 2.5 | 4.4 | 4.1 | 2.2 | 1.1 |
| strain (%)   value after 7 days | 2.5 | 4.1 | 4.0 | 2.1 | 0.9 |
| Shore A   initial value | 11.0 | 8.1 | 6.8 | 7.6 | 12.3 |
| hardness   value after 7 days | 11.1 | 8.3 | 6.8 | 7.7 | 12.5 |
| degree of coloration (ΔE*) | 6.4 | 7.8 | 5.9 | 8.5 | 7.6 |
| removability | A | A | A | A | A |
| machinability | A | A | A | A | A |

Comparative Example 1

A test was made on an acrylic tissue conditioner consisting of 120 parts by weight of ethyl methacrylate, 85 parts by weight of butyl phthalyl butyl glycolate and 15 parts by weight of ethanol in accordance with the above evaluation method. The result is shown in Table 5.

Comparative Example 2

A test was made on an acrylic tissue conditioner consisting of 110 parts by weight of a copolymer of butyl methacrylate (90 mol %) and ethyl methacrylate (10 mol %) and 100 parts by weight of butyl phthalyl butyl glycolate in accordance with the above evaluation method. The result is shown in Table 5.

Comparative Examples 3 and 4

The materials of each composition shown in Table 5 were mixed in a planetary in the same manner as in Example 1 to prepare pastes. The platinum catalyst used was the same as one used in Example 1.

TABLE 5

|  | Comp. Ex. 1 | Comp. Ex. 2 | Comp. Ex. 3 | Comp. Ex. 4 |
|---|---|---|---|---|
| (I) component (A) |  |  | a1 50 a3 50 | a1 25 a3 75 |
| component (C) |  |  | c1 50 | c2 30 |
| component (D) (ppm) |  |  | 100 | 50 |
| other component |  |  | TiO2 pigment 1 |  |

TABLE 5-continued

|  |  | Comp. Ex. 1 | Comp. Ex. 2 | Comp. Ex. 3 | Comp. Ex. 4 |
|---|---|---|---|---|---|
| (II) | component (A) |  |  | a1 50 a3 50 | a1 50 a3 50 |
|  | component (B) (H/V ratio) |  |  | b2 5.1 (2.0) | b1 0 (0.0) |
|  | component (E) (H/V ratio) |  |  | 0 (0.0) | e1 1.8 (0.7) |
|  | total H/V ratio |  |  | (2.0) | (0.7) |
|  | component (C) |  |  | c1 50 | c2 30 |
|  | other component |  |  |  |  |
|  | mixing ratio ((I)/(II)) |  |  | 1:1 | 1:1 |
| tan δ |  | 1.0 | 0.9 | 0.3 | — |
| elastic | initial value | 34 | 32 | 13 | — |
| strain (%) | value after 7 days | 20 | 21 | 13 | — |
| permanent | initial value | 3.7 | 3.0 | 0.3 | — |
| strain (%) | value after 7 days | 1.7 | 1.2 | 0.3 | — |
| Shore A | initial value | 11 | 12 | 20 | — |
| hardness | value after 7 days | 16 | 17 | 20 | — |
| degree of coloration (ΔE*) |  | 29 | 30 | 7.4 | — |
| removability |  | C | C | A | — |
| machinability |  | B | B | A | — |

Comp. Ex.: Comparative Example

As is clear from the results shown in Tables 3, 4 and 5, the dental tissue conditioners of the present invention (Examples 1 to 10) retains sufficient loss tangent (tan δ), elastic strain, permanent strain and Shore A hardness throughout the first seven days of its use, has a small degree of coloration and can be easily removed from a spent denture base.

Comparing Example 1 with Example 4 and Example 3 with Example 5, while a change in the total H/V ratio between Example 1 and Example 4 and one between Example 3 and Example 5 are both in the range of 1.0 to 1.2, changes in the properties of the cured products of Examples 3 and 5, in which the component (E) was further contained, are smaller than those of Examples 1 and 4. That is, it is understood that the viscoelasticities (such as elastic strain, permanent strain, loss tangent and Shore A hardness) of the cured products of Examples 3 and 5 are easier to control.

On the other hand, although the acrylic tissue conditioners (Comparative Examples 1 and 2) have sufficient loss tangent (tan δ), elastic strain, permanent strain and Shore A hardness at the beginning of its use, those properties lower with time. Further, they have a large degree of coloration and are difficult to remove from a spent denture base. It is understood from this that the dental tissue conditioner of the present invention is excellent in durability and workability.

Further, it is understood from Comparative Example 3 that the cured product shows a poor viscoelasticity when the amount of the component (B) mixed exceeds the required amount. In addition, it is understood from Comparative Example 5 that without the component (B), a curing reaction does not take place, with the result of an improper tissue conditioner.

What is claimed is:

1. A method of employing dental tissue conditioner which comprises the steps of applying a silicone rubber-based dental tissue conditioner composition to a denture base and curing the denture in the mouth of a patient to provide a temporary denture, and, subsequent to use of the temporary denture, removing the dental tissue conditioner composition from said denture.

2. The method of claim 1, wherein the silicone rubber is formed by the addition polymerization carried out at room temperature.

3. The method of claim 1, wherein the silicone rubber is a cured product of an uncured composition which comprises:

(A) an organopolysiloxane having at least two organic groups having a terminal carbon-carbon unsaturated bond in the molecule, (B) an organohydrogenpolysiloxane having at least three hydrogen atoms, which are directly bonded to silicone atoms, in the molecule, and (D) a hydrosilylation catalyst;

the ratio of the total number of the hydrogen atoms, which are directly bonded to silicone atoms, of the component (B) to the total number of the terminal carbon-carbon unsaturated bonds of the component (A) being 0.2 to 1.5.

4. The method of claim 1, wherein the silicone rubber is a cured product of an uncured composition which comprises:

(A) an organopolysiloxane having at least two organic groups having a terminal carbon-carbon unsaturated bond in the molecule, (B) an organohydrogenpolysiloxane having at least three hydrogen atoms, which are directly bonded to silicone atoms, in the molecule, (D) a hydrosilylation catalyst, (E) an organohydrogenpolysiloxane having one or two hydrogen atoms, which are directly bonded to silicone atoms, in the molecule;

the ratio of the total number of the hydrogen atoms, which are directly bonded to silicone atoms, of the component (B) and the hydrogen atoms, which are directly bonded to silicone atoms, of the component (E) to the total number of the terminal carbon-carbon unsaturated bonds of the component (A) being 0.5 to 5; and the ratio of the total number of the hydrogen atoms, which are directly bonded to silicone atoms, of the component (E) to the total number of the hydrogen atoms, which are directly bonded to silicone atoms, of the component (B) being 0.5 to 10.

5. The method of claim 1, wherein the material for dental tissue conditioner is a silicone rubber composition which further contains a filler in addition to the silicone rubber.

6. The method of claim 5, wherein the silicone rubber composition has an elastic strain of 15% or more and a permanent strain of 0.5% or more.

7. The method of claim 5, wherein the silicone rubber composition has a loss tangent of 0.5 or more.

8. The method of claim 5, wherein the silicone rubber composition has a Shore A hardness of 15 or less.

9. The method of claim 5, wherein the silicone rubber composition is a cured product of an uncured composition which comprises:

(A) an organopolysiloxane having at least two organic groups having a terminal carbon-carbon unsaturated bond in the molecule, (B) an organohydrogenpolysiloxane having at least three hydrogen atoms, which are directly bonded to silicone atoms, in the molecule, (C) at least one filler selected from the group consisting of silicone resin particles and silica particles, and (D) a hydrosilylation catalyst;

the ratio of the total number of the hydrogen atoms, which are directly bonded to silicone atoms, of the component (B) to the total number of the terminal carbon-carbon unsaturated bonds of the component (A) being 0.2 to 1.5; the component (C) being contained in an amount of 1 to 300 parts by weight per 100 parts by weight of the component (A); and the component (D) being contained in a catalytic amount.

10. The method of claim 5, wherein the silicone rubber composition is a cured product of an uncured composition which comprises:

(A) an organopolysiloxane having at least two organic groups having a terminal carbon-carbon unsaturated bond in the molecule, (B) an organohydrogenpolysiloxane having at least three hydrogen atoms, which are directly bonded to silicone atoms, in the molecule, (C) at least one filler selected from the group consisting of silicone resin particles and silica particles, (D) a hydrosilylation catalyst, and (E) an organohydrogenpolysiloxane having one or two hydrogen atoms, which are directly bonded to silicone atoms, in the molecule;

the ratio of the total number of the hydrogen atoms, which are directly bonded to silicone atoms, of the component (B) and the hydrogen atoms, which are directly bonded to silicone atoms, of the component (E) to the total number of the terminal carbon-carbon unsaturated bonds of the component (A) being 0.5 to 5; the ratio of the total number of the hydrogen atoms, which are directly bonded to silicone atoms, of the component (E) to the total number of the hydrogen atoms, which are directly bonded to silicone atoms, of the component (B) being 0.5 to 10; the component (C) being contained in an amount of 1 to 300 parts by weight per 100 parts by weight of the component (A); and the component (D) being contained in a catalytic amount.

11. A dental tissue conditioner kit, in which a first uncured composition component comprising:

(A) an organopolysiloxane having at least two organic groups having a terminal carbon-carbon unsaturated bond in the molecule, (B) an organohydrogenpolysiloxane having at least three hydrogen atoms, which are directly bonded to silicone atoms, in the molecule, and optionally, (E) an organohydrogenpolysiloxane having one or two hydrogen atoms, which are directly bonded to silicone atoms, in the molecule, and a second uncured composition component comprising:

(A) an organopolysiloxane having at least two organic groups having a terminal carbon-carbon unsaturated bond in the molecule, and (D) a hydrosilylation catalyst are filled in separate containers; and at least one of the first uncured composition component and the second uncured composition component contains:

(C) at least one filler selected from the group consisting of silicone resin particles and silica particles.

12. The kit of claim 11, wherein both the first uncured composition component and the second uncured composition component are a paste.

* * * * *